(12) United States Patent
Qiu et al.

(10) Patent No.: US 11,791,017 B2
(45) Date of Patent: Oct. 17, 2023

(54) SOYBEAN ANTI-POD-SHATTERING MAJOR QTLQPD05, AND MAPPING METHOD AND APPLICATION THEREOF

(71) Applicant: INSTITUTE OF CROP SCIENCES, CHINESE ACADEMY OF AGRICULTURAL SCIENCES, Beijing (CN)

(72) Inventors: Lijuan Qiu, Beijing (CN); Dezhi Han, Beijing (CN); Jianan Han, Beijing (CN); Hongrui Yan, Beijing (CN); Bohong Su, Beijing (CN)

(73) Assignee: Institute of Crop Sciences, Chinese Academy of Agricultural Sciences, Beijing (CN)

( * ) Notice: Subject to any disclaimer, the term of this patent is extended or adjusted under 35 U.S.C. 154(b) by 1087 days.

(21) Appl. No.: 16/392,053

(22) Filed: Apr. 23, 2019

(65) Prior Publication Data

US 2019/0333602 A1     Oct. 31, 2019

(30) Foreign Application Priority Data

Apr. 24, 2018     (CN) .......................... 201810375333.0

(51) Int. Cl.
| | | |
|---|---|---|
| G16B 20/40 | (2019.01) | |
| G16B 20/20 | (2019.01) | |
| G16B 40/10 | (2019.01) | |
| C12Q 1/6895 | (2018.01) | |
| C12Q 1/6897 | (2018.01) | |
| C12Q 1/6869 | (2018.01) | |

(52) U.S. Cl.
CPC ........... *G16B 20/40* (2019.02); *C12Q 1/6895* (2013.01); *C12Q 1/6897* (2013.01); *G16B 20/20* (2019.02); *G16B 40/10* (2019.02); *C12Q 1/6869* (2013.01); *C12Q 2600/13* (2013.01); *C12Q 2600/158* (2013.01)

(58) Field of Classification Search
None
See application file for complete search history.

(56) References Cited

FOREIGN PATENT DOCUMENTS

CN     101501217 A     8/2009

OTHER PUBLICATIONS

Kang et al. Population-specific QTLs and their different epistatic interactions for pod dehiscence in soybean Euphytica (2009) 166: 15-24 DOI 10.1007/s10681-008-9810-6.*
Han et al. Population-specific QTLs and their diVerent epistatic interactions for pod dehiscence in soybean Theoretical and Applied Genetics https://doi.org/10.1007/s00122-019-03352-x.*
Liu et al. QTL Mapping of Domestication-related Traits in Soybean (Glycine max) Annals of Botany 100: 1027-1038, 2007 doi: 10.1093/aob/mcm149.*
Han et al. QTL Mapping of Domestication-related Traits in Soybean (Glycine max) Euphytica (2021) 217:120 https://doi.org/10.1007/s10681-021-02838-4.*
Fuller, D.Q., Contrasting Patterns in Crop Domestication and Domestication Rates: Recent Archaeobotanical Insights from the Old World, Annals of Botany, vol. 100, Issue 5, Oct. 2007, pp. 903-924.
Hancock, J.F., Plant Evolution and the Origin of Crop Species, Oxford University Press; 2nd edition (Jan. 8, 2004).
Harlan, J.R., et al., Comparative Evolution of Cereals, Evolution, vol. 27, No. 2 (Jun. 1973), pp. 311-325.
Funatsuki, H., et al., Mapping and use of QTLs controlling pod dehiscence in soybean, Breeding Science 61: 554-558 (2012).
Christiansen, L.C., Examination of the dehiscence zone in soybean pods and isolation of a dehiscence-related endopolygalacturonase gene, Plant, Cell and Environment (2002) 25, 479-490.
Funatsuki, H., et al., Molecular basis of a shattering resistance boosting global dissemination of soybean, PNAS, Dec. 2, 2014, 111 (50) 17797-17802.
Bailey, M.A., et al., Pod Dehiscence of Soybean: Identification of Quantitative Trait Loci, Journal of Heredity, vol. 88, Issue 2, Mar./Apr. 1997, pp. 152-154.
Funatsuki, H., et al., Simple sequence repeat markers linked to a major QTL controlling pod shattering in soybean, Plant Breeding 125, 195-197 (2006).
Kang, S.T., et al., Genetic Analysis of Pod Dehiscence in Soybean, Korean J. Crop Sci. 50(4): 281-285(2005).
Dong, Y., et al., Pod shattering resistance associated with domestication is mediated by a NAC gene in soybean, Nature Communications vol. 5, Article No. 3352 (2014).
Kang, S.T., et al., Population-speciWc QTLs and their diVerent epistatic interactions for pod dehiscence in soybean [*Glycine max* (L.) merr], Euphytica (2009) 166:15-24.
Han, D., et al., Occurrence characteristics and molecular genetic basis of pod shattering in soybean, Hereditas (Beijing), 2015, vol. 37, Issue (6): 535-543.

(Continued)

*Primary Examiner* — Joseph Woitach
(74) *Attorney, Agent, or Firm* — AVEK IP, LLC

(57) ABSTRACT

The present invention provides a soybean anti-pod-shattering major QTLqPD05, and a mapping method and application thereof, and belongs to the field of QTL mapping. The soybean anti-pod-shattering major QTL is mapped on the chromosome 5 of soybean at a physical position between 40448596-40703417. For the method for mapping the soybean anti-pod-shattering major QTL, a SLAF marker is screened at the whole genome level of the soybean by utilizing a SLAF-seq sequencing technology, so as to explore the QTLs related to pod shattering from this population. By using a material of a RIL7 population which has pod-shattering soybean and anti-pod-shattering soybean as the parents, a high-density genetic linkage map covering the whole genome of soybean is constructed, and QTL mapping of the anti-pod-shattering trait is carried out on this population to obtain QTLs related to anti-pod-shattering. In addition to this, the construction of the high-density genetic linkage map and the identification of the novel QTLs related to anti-pod-shattering specific to this population provide a reference for efficient QTL mapping of soybean.

8 Claims, 7 Drawing Sheets

Specification includes a Sequence Listing.

(56) References Cited

OTHER PUBLICATIONS

Saghai-Maroof, M.A., Ribosomal DNA spacer-length polymorphisms in barley: Mendelian inheritance, chromosomal location, and population dynamics, Proc. Natl. Acad. Sci., vol. 81, pp. 8014-8018, Dec. 1984.

Peng, Y., et al., Preliminary analysis of soybean pod-shattering in Huanghuai river basin, Soybean Science, vol. 10, No. 4, Nov. 1991.

Han, J., et al., Development and Application of Related Markers of Soybean Pod-Shattering, Tenth National Soybean Symposium, Beijing, China, Jul. 31, 2017.

\* cited by examiner

SOYBEAN ANTI-POD-SHATTERING MAJOR QTLQPD05, AND MAPPING METHOD AND APPLICATION THEREOF

CROSS REFERENCE TO RELATED APPLICATIONS

This application claims priority to Chinese application number 20181037533-3.0, filed Apr. 24, 2018, the disclosure of which is incorporated by reference herein in its entirety.

FIELD OF THE DISCLOSURE

The disclosure relates generally to the field of QTL mapping. More specifically, the disclosure relates to the field of soybean anti-pod-shattering major QTLqPD05, and a mapping method and application thereof.

BACKGROUND

Pod shattering is essential for the seed dispersal of a wild plant having pods. For a wild plant, seed dispersal is a necessary process for the survival and reproduction of the wild plant, which provides the future generations with sufficient growth space and the chance to survive under different environmental conditions (Fuller 2007). However, in cultivated crops, pod shattering results in severe yield reduction, since seeds cannot be harvested due to pod shattering. During planting and harvesting by farmers, it is desirable to retain pods prior to harvesting, and anti-pod shattering is a trait of unconscious selection associated with crop yield (Hancock and Hancock 2003; Harlan et al. 1973). Therefore, anti-pod shattering is an important domestication trait during crop domestication (Hideyuki et al. 2012). Although we strictly screened during crop domestication to avoid pod shattering, pod shattering before harvesting is still a problem that needs to be addressed urgently in breeding (Christiansen et al. 2002). Although crop anti-pod-shattering have made great progress in genetic breeding, we know little about the gene for crop anti-pod-shattering (Funatsuki et al. 2014).

Over the past 20 years, a series of QTL loci associated with soybean pod shattering have been identified. So far, a large number of studies have used RFLP (Bailey et al. 1997), SSR markers (Funatsuki et al. 2006) and the like methods to map QTLs associated with soybean pod shattering by means of recombinant inbred lines, indicating that soybean pod shattering is controlled by the major QTL and some minor QTLs. Since different genes control pod shattering due to the different genetic backgrounds of a population, the anti-pod-shattering characteristic is embodied as controlled by a single recessive major gene or multiple genes (Kang et al. 2005). Bailey et al. first discovered a major QTL existed on chromosome 16 using recombinant inbred lines (RILS) and found some minor QTLs respectively on chromosomes 2, 15, and 19 (Bailey et al. 1997), and after fine mapping, the candidate gene Glyma16g25580 controls the pod shattering and is named as Pdh1 (Pod dehiscence 1) (Funatsuki et al. 2014). At the same time, the study found that a major NAC gene in soybean, i.e., Glyma.16g019400, named as SHAT1-5, also regulates soybean pod shattering (Dong et al. 2014). Through two sets of RILs, Kang et al. remapped three new minor QTLs on chromosomes 5, 10 and 14 using an SSR marker (Kang et al. 2009).

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

In some embodiments, an objective is to provide a novel soybean anti-pod-shattering major QTLqPD05, and a mapping method and application thereof, such that the anti-pod-shattering major QTL has good stability.

According to an embodiment, the invention provides a soybean anti-pod-shattering major QTLqPD05, where the major QTL is mapped on the chromosome 5 of soybean at a physical position between 40448596-40703417; and the genetic distance of 40448596-40703417 is 29.653-30.04 cM.

According to another embodiment, the invention provides a method for mapping the above soybean anti-pod-shattering major QTLqPD05, including the following steps. (1) Constructing recombinant inbred lines of the fifth and sixth generations by using pod-shattering soybean and anti-pod-shattering soybean as parents, simultaneously sowing the pod-shattering soybean, the anti-pod-shattering soybean and the recombinant inbred line of the fifth-generation, and simultaneously sowing the pod-shattering soybean, the anti-pod-shattering soybean and the recombinant inbred line of the sixth-generation, to obtain samples of the pod-shattering soybean, the anti-pod-shattering soybean and the soybean recombinant inbred lines in two years. (2) Respectively extracting DNAs from samples of the pod-shattering soybean, the anti-pod-shattering soybean and the soybean recombinant inbred lines in the two years, to obtain genomic DNAs of the pod-shattering soybean, the anti-pod-shattering soybean and the soybean recombinant inbred lines. (3) Respectively constructing SLAF libraries by utilizing the genomic DNA of each of the samples of the pod-shattering soybean, the anti-pod-shattering soybean and the soybean recombinant inbred lines, and separately sequencing the constructed SLAF libraries to obtain original sequencing data. (4) Filtering the original sequencing data to select 4-103 bp in the middle of each reads as the analysis data. (5) Aligning the analysis data to a reference genome, where each reads that has paired ends aligned to a reads at the same position is of the same SLAF tag, and then conducting polymorphic analysis of the SLAF tags according to the differences in the number of alleles and the gene sequences to obtain polymorphic SLAF tags. (6) Filtering the polymorphic SLAF tags to obtain screened polymorphic SLAF tags; where the filtering is to delete the polymorphic SLAF tags having the following conditions: a. a polymorphic SLAF tag having a parent sequencing depth below 10×; b. a polymorphic SLAF tag containing more than 5 SNP loci; and c. a polymorphic SLAF tag that is insufficient to cover 70% of genotype individuals in all progenies. (7) Aligning the screened polymorphic SLAF tags with a reference genome for mapping, where the screened polymorphic SLAF tags are mapped to 20 chromosomes, and using each chromosome as a linkage group to calculate a genetic distance between adjacent polymorphic SLAF tags on each linkage group, so as to obtain a high-density genetic map. (8) Conducting QTL mapping of the pod-shattering phenotypes and pod-shattering traits of soybeans in the two years by employing an inclusive composite interval mapping method according to the high-density genetic map, so as to obtain the interval of the soybean anti-pod-shattering major QTLs.

It may be desirable that the number of the samples of soybean recombinant inbred lines in step (2) is 200-300.

It may be desirable that in step (1) the pod-shattering soybean is used as the male parent; and the anti-pod-shattering soybean is used as the female parent.

It may be desirable that the variety of the pod-shattering soybean is Heihe 18; and the variety of the anti-pod-shattering soybean is Heihe 43.

It may be desirable that in step (3), during the separate sequencing the sequencing depth of the SLAF library of the pod-shattering soybean is 39.74×; the sequencing depth of the SLAF library of the anti-pod-shattering soybean is 34.87×; and the sequencing depth of the SLAF library of the soybean recombinant inbred line is 12.35×.

It may be desirable that in step (4), the filtration criteria are as follows: filtering out a reads containing a linker sequence; and filtering out a reads having a N content exceeding 10% of the length of the reads.

It may be desirable that in step (7), before the calculation of the genetic distance, the method further includes performing second filtering on the polymorphic SLAF tags; where the criterion for the second filtering is to calculate an MLOD value between pairwise polymorphic SLAF tags, and then filter out polymorphic SLAF tags each with a MLOD value below 5.

According to a further embodiment, the invention provides an application of the above soybean anti-pod-shattering major QTL or a soybean anti-pod-shattering major QTL obtained by the above mapping method in studying the genetic mechanism of the pod-shattering trait or the screening for molecular markers related to soybean yield.

It may be desirable that the molecule marker is a CAPS molecule marker; the amplification primer for the CAPS molecule marker includes a forward primer and a reverse primer; the forward primer has a nucleotide sequence as shown in SEQ ID NO. 1 of the Sequence Listing; and the reverse primer has a nucleotide sequence as shown in SEQ ID NO. 2 of the Sequence Listing.

In some embodiments, the invention provides the application of the soybean anti-pod-shattering major QTLqPD05 in map-based cloning.

In embodiments, the invention provides the application of the soybean anti-pod-shattering major QTLqPD05 in transgenic breeding of a pod-shattering gene.

In embodiments, the invention provides a soybean anti-pod-shattering gene obtained by screening based on the soybean anti-pod-shattering major QTLqPD05, including a DNA (cytosine-5) methyltransferase 3 coding sequence, a NAPD-dependent malic enzyme coding sequence, and a hypothetical protein coding sequence. The DNA (cytosine-5) methyltransferase 3 coding sequence includes the following nucleotide sequences: (1) a nucleotide sequence included as shown in SEQ ID No. 3 of Sequence Listing; and (2) a nucleotide sequence obtained by nucleotide substitution, deletion and addition on the basis of the condition (1). The NAPD-dependent malic enzyme coding sequence includes the following nucleotide sequences: (a) a nucleotide sequence included as shown in SEQ ID No. 4 of Sequence Listing; and (b) a nucleotide sequence obtained by nucleotide substitution, deletion and addition on the basis of the condition (a). The hypothetical protein coding sequence includes the following nucleotide sequences: (I) a nucleotide sequence included as shown in SEQ ID No. 29 of Sequence Listing; and (II) a nucleotide sequence obtained by nucleotide substitution, deletion and addition on the basis of the condition (I).

In embodiments, the invention provides the application of the soybean anti-pod-shattering gene or its modified version in selection of anti-pod-shattering varieties of soybean.

In embodiments, the invention provides a soybean anti-pod-shattering major QTLqPD05, the qPD05 is mapped on the chromosome 5 of soybean at a physical position between 40448596-40703417; and the genetic distance of 40448596-40703417 is 29.653-30.04 cM. Since the yield of soybean is positively correlated with the anti-pod shattering rate, it is possible to significantly improve the rate of anti-pod-shattering by detecting the soybean anti-pod-shattering major QTL and thus screening the varieties having the anti-pod-shattering major QTL. Therefore, mapping the major QTL is a breeding process for further detecting the anti-pod-shattering trait of soybean and thus improving the soybean yield and improving good soybean varieties.

In embodiments, the invention provides a method for mapping the soybean anti-pod-shattering major QTLqPD05. In the invention a SLAF marker screened at the whole genome level of the soybean by utilizing a SLAF-seq sequencing technology, so as to explore the QTLs related to pod shattering from this population. By using a material of a RIL7 population which has pod-shattering soybean and anti-pod-shattering soybean as the parents, a high-density genetic linkage map covering the whole genome of soybean is constructed, and QTL mapping of the anti-pod-shattering trait is carried out on this population to obtain QTLs related to anti-pod-shattering. In addition to this, the construction of the high-density genetic linkage map and the identification of the novel QTLs related to anti-pod-shattering specific to this population provide a reference for efficient QTL mapping of soybean.

BRIEF DESCRIPTION OF THE DRAWINGS

Illustrative embodiments of the present disclosure are described in detail below with reference to the attached drawing figures.

FIG. 1 is a phenotypic distribution diagram showing a pod-shattering rate of a RIL population, wherein

DETAILED DESCRIPTION

Figure 1A:
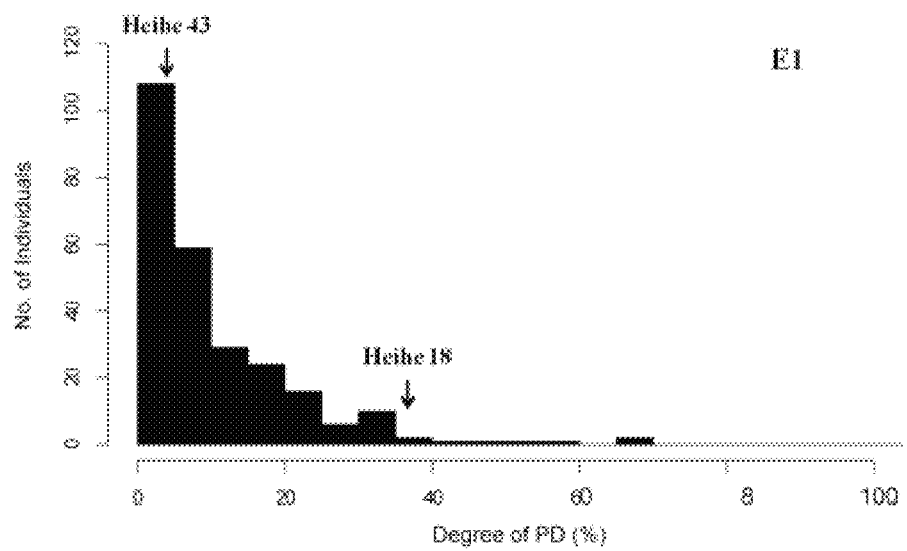
FIG. 1A shows the pod-shattering rates of 260 RILs and two parents thereof in Heihe of Heilongjiang Province in 2015.

According to an embodiment, the invention provides a soybean anti-pod-shattering major QTLqPD05, the qPD05 is mapped on the chromosome 5 of soybean at a physical position between 40448596-40703417; and the genetic distance of 40448596-40703417 is 29.653-30.04 cM.

According to another embodiment, the soybean anti-pod-shattering major QTL has a LOD (logarithm of the odds) score of 7.171; an ADD (additive effect) value of −5.995, and a PVE (phenotypic variation explained) of 15.138%.

The soybean anti-pod-shattering major QTLs were detected in both 2015 and 2016, and thus may be considered as stable QTLs.

According to a further embodiment, the invention provides a method for mapping the soybean anti-pod-shattering major QTL, including the following steps. (1) Constructing recombinant inbred lines of the fifth and sixth generations by using pod-shattering soybean and anti-pod-shattering soybean as parents, simultaneously sowing the pod-shattering soybean, the anti-pod-shattering soybean and the recombinant inbred line of the fifth-generation, and simultaneously sowing the pod-shattering soybean, the anti-pod-shattering soybean and the recombinant inbred line of the sixth-generation, to obtain samples of the pod-shattering soybean, the anti-pod-shattering soybean and the soybean recombinant inbred lines in two years. (2) Respectively extracting DNAs from samples of the pod-shattering soybean, the anti-pod-shattering soybean and the soybean recombinant inbred lines in the two years, to obtain genomic DNAs of the pod-shattering soybean, the anti-pod-shattering soybean and the soybean recombinant inbred lines. (3) Respectively constructing SLAF libraries by utilizing the genomic DNAs of the pod-shattering soybean, the anti-pod-shattering soybean and the soybean recombinant inbred lines, and separately sequencing the constructed SLAF libraries to obtain original sequencing data. (4) Filtering the original sequencing data to select 4-103 bp in the middle of each reads as the analysis data. (5) Aligning the analysis data to a reference genome, where each reads that has paired ends aligned to a reads at the same position is of the same SLAF tag, and then conducting polymorphic analysis of the SLAF tags according to the differences in the number of alleles and the gene sequences to obtain polymorphic SLAF tags. (6) Filtering the polymorphic SLAF tags to obtain screened polymorphic SLAF tags; where the filtering is to delete the polymorphic SLAF tags having the following conditions: a. a polymorphic SLAF tag having a parent sequencing depth below 10×; b. a polymorphic SLAV tag containing more than 5 SNP loci; and c. a polymorphic SLAF tag that is insufficient to cover 70% of genotype individuals in all progenies. (7) Aligning the screened polymorphic SLAF tags with a reference genome for mapping, where the screened polymorphic SLAF tags are mapped to 20 chromosomes, and using each chromosome as a linkage group to calculate a genetic distance between adjacent polymorphic SLAF tags on each linkage group, so as to obtain a high-density genetic map. (8) Conducting QTL mapping of the pod-shattering phenotypes and pod-shattering traits of soybeans in the two years by employing an inclusive composite interval mapping method according to the high-density genetic map, so as to obtain the interval of the soybean anti-pod-shattering major QTLs.

According to an alternate embodiment, recombinant inbred lines (RILs) of the fifth and sixth generations are constructed by using pod-shattering soybean and anti-pod-shattering soybean as parents; the pod-shattering soybean, the anti-pod-shattering soybean and the recombinant inbred line of the fifth-generation are sowed simultaneously; and the pod-shattering soybean, the anti-pod-shattering soybean and the recombinant inbred line of the sixth-generation are sowed simultaneously, to obtain samples of the pod-shattering soybean, the anti-pod-shattering soybean and the soybean recombinant inbred lines in two years.

In embodiments, the pod-shattering soybean may be used as the male parent; and the anti-pod-shattering soybean may be used as the female parent. The variety of the anti-pod-shattering soybean may be Heihe 43; and the variety of the pod-shattering soybean may be Heihe 18. In the invention, the pod-shattering soybean and the anti-pod-shattering soybean are subjected to phenotype identification. The main evaluation index for the identification of soybean pod-shattering phenotypes is the pod-shattering rate. The pod-shattering rate=(the number of shattered pods/the number of total pods)×100% (Preliminary analysis of the pod-shattering of soybean in Huanghuai area, Peng Yuhua, Soybean Science, 1991). Asian Vegetable Research and Development Center (AVRDC) graded the pod-shattering phenotypes of soybean based on the pod-shattering rates, where the pod-shattering rate of 0% was set as grade 1 (high anti-pod-shattering), the pod-shattering rate between 0-10% was set as grade 2 (anti-pod-shattering), the pod-shattering rate between 11-25% was set as grade 3 (moderate anti-pod-shattering), the pod-shattering rate between 26-50% was set as grade 4 (moderate pod-shattering), and the pod-shattering rate above 50% was set as grade 5 (serious pod-shattering).

In embodiments, the invention may employ an indoor drying method to determine the pod-shattering rate. In order to ensure the reliability of the data, it is avoided to touch the pods when samples are picked, so as to keep the consistency of the test materials before detection as far as possible. The indoor drying method includes the following steps: setting the temperature to 80° C. and setting the drying time to 5 h as the optimum detection conditions for identifying the pod-shattering rate. The difference in the pod-shattering rate between Heihe 18 and Heihe 43 is extremely significant during manual detection. According to the AVRDC evaluation criteria, the Heihe 43 has the pod-shattering of Grade 2 (medium anti-pod-shattering), and the Heihe 18 has the pod-shattering of Grade 4 (medium pod-shattering), which is substantially consistent with the natural pod-shattering conditions.

The invention has no specific limitation on the method for constructing the recombinant inbred lines of the fifth and sixth generations, and a method for constructing a recombinant inbred line which is well known in the art may be employed.

In embodiments, the samples of the pod-shattering soybean, the anti-pod-shattering soybean and the soybean recombinant inbred line of the fifth generation were planted in a geographical environment of Heilongjiang in 2015, and the samples of the pod-shattering soybean, the anti-pod-shattering soybean and the soybean recombinant inbred line of the sixth generation were planted in the geographical environment of Heilongjiang in 2016, so as to obtain samples of the pod-shattering soybean, the anti-pod-shattering soybean and the soybean recombinant inbred lines during the two years, respectively. The geographical environments of Heilongjiang are the same.

In embodiments, after the samples of the pod-shattering soybean, the anti-pod-shattering soybean and the soybean recombinant inbred lines in the two years are obtained, genomic DNAs are respectively extracted from each sample of the pod-shattering soybean, the anti-pod-shattering soybean and the soybean recombinant inbred lines in the two years, to obtain genomic DNAs of the pod-shattering soybean, the anti-pod-shattering soybean and the soybean recombinant inbred lines.

In embodiments, the samples of the pod-shattering soybean, the anti-pod-shattering soybean and the soybean recombinant inbred lines are planted in the same environment for two years, so as to obtain the samples of the pod-shattering soybean, the anti-pod-shattering soybean and the soybean recombinant inbred lines during the two years, respectively. In the invention, it may be desirable that statistics of the respective pod-shattering phenotypes of the samples of the pod-shattering soybean, the anti-pod-shattering soybean and the soybean recombinant inbred lines during the two years is carried out for later QTL mapping.

In embodiments, the raw material for DNA extraction may be a leaf of a soybean sample. The invention has no specific limitation on the DNA extraction method, and an extraction method well known in the art may be employed. In the invention, the number of the samples of soybean recombinant inbred lines may be 200-300, and preferably 260. The extracted DNA may be subjected to quality detection. The quality detection includes determination of DNA integrity and concentration of extracted DNA. The DNA integrity assay may be performed by employing detection through gel electrophoresis. The determination of the concentration of extracted DNA may be carried out by using a nucleic acid protein quantitative detector.

In embodiments, after the extracted DNA is obtained, a SLAF library is constructed by utilizing the genomic DNA of each of the samples of the pod-shattering soybean, the anti-pod-shattering soybean and the soybean recombinant inbred lines, and the constructed SLAF libraries are sequenced separately to obtain original sequencing data.

The invention has no specific limitation on the method for constructing the SLAF library, and a solution for constructing a SLAF library well known in the art may be employed. In order to ensure accuracy during the construction of the SLAF library, it may be desirable to use the soybean Williams 82 v2.1 genome (phytozome.jgi.doe.gov) as a reference genome for enzyme digestion. The type of the enzyme for enzyme digestion may be a combination of RsaI enzyme digestion and HaeIII enzyme digestion. In the invention, the SLAF libraries may be constructed by conducting enzyme digestion of the genomic DNA of each sample to construct a library separately. A sequence having an enzyme-digested fragment length of 364-414 bp is defined as a SLAF tag, and it is predicted that 132,516 SLAF tags may be obtained in each library.

In embodiments, after the SLAF library is constructed, it may be desirable that Illumina HiSeq is used for sequencing of paired ends (125 bp). In the invention, the sequencing depth of the SLAF library of the pod-shattering soybean may be 39.74×; the sequencing depth of the SLAF library of the anti-pod-shattering soybean may be 34.87×; and the sequencing depth of the SLAF library of the soybean recombinant inbred line may be 12.35×.

In order to evaluate the accuracy of the library-construction experiment, the invention may use *Oryza sativa* L *japonica* as a control to be subjected to the same treatment and participate in library construction and sequencing. The enzyme digestion efficiency is evaluated by the alignment efficiency of the control data, so as to judge the accuracy and effectiveness of the original sequencing data.

After the original sequencing data is obtained, the invention filters the original sequencing data to select 4-103 bp in the middle of each reads as the analysis data.

In embodiments, the filtration criteria may be as follows: filtering out a reads containing a linker sequence; and filtering out a reads having a N content exceeding 10% of the length of the reads.

In embodiments, after the analysis data is obtained, the analysis data is aligned to the reference genome, where each reads that has paired ends aligned to a reads at the same position is of the same SLAF tag, and then polymorphic analysis of the SLAF tags is conducted according to the differences in the number of alleles and the gene sequences to obtain polymorphic SLAF tags.

In embodiments, the software used for aligning the analysis data to the reference genome may be the BWA software. The polymorphism analysis method may be carried out by using the BWA software.

In embodiments, in order to facilitate subsequent genetic analysis, the invention conducts genotype encoding of the polymorphic SLAF tags. The genotype encoding method may be dividing the polymorphic tags into eight separation models (ab×cd, ef×eg, hk×hk, lm×ll, nn×np, aa×bb, ab×cc, and cc×ab) according to the biallelic encoding rule commonly used in genetics. RIL indicates that it is suitable for the type of aa×bb.

In embodiments, After the polymorphic SLAF tags are obtained, the polymorphic SLAF tags are filtered to obtain screened polymorphic SLAF tags; where the filtering of the polymorphic SLAF tags is to delete the polymorphic SLAF tags having the following conditions: a. a polymorphic SLAF tag having a parent sequencing depth below 10×; b. a polymorphic SLAF tag containing more than 5 SNP loci; and c. a polymorphic SLAF tag that is insufficient to cover 70% of genotype individuals in all progenies.

In embodiments, the filtering may be beneficial for ensuring the improvement in the quality of the constructed genetic map.

In embodiments, after the screened polymorphic SLAF tags are obtained, the screened polymorphic SLAF tags are aligned to the reference genome for mapping, where the screened polymorphic SLAF tags are mapped to 20 chromosomes, and by using each chromosome as a linkage group, a genetic distance between adjacent polymorphic SLAF tags on each linkage group is calculated so as to obtain a high-density genetic map.

In embodiments, before the calculation of the genetic distance, the method may further include performing second filtering on the polymorphic SLAF tags; where the criterion for the second filtering is to calculate an MLOD value between pairwise polymorphic SLAF tags, and then filter out polymorphic SLAF tags each with a MLOD value below 5. The second filtering facilitates obtaining of Markers, thereby depicting a high-density genetic linkage map.

In embodiments, QTL mapping is conducted according to the pod-shattering phenotypes and pod-shattering traits of soybeans in the two years by employing an inclusive composite interval mapping method, so as to obtain the interval of the soybean anti-pod-shattering major QTLs.

In embodiments, the software for the inclusive composite interval mapping method may be a R/qtl software. The inclusive composite interval mapping method performs threshold setting by using a permutation test for 1000 times, where firstly a LOD threshold corresponding to the confidence of 0.99 is considered, and if there is no mapped interval, then a LOD threshold corresponding to the confidence of 0.95 is considered; and if there is no mapped interval, then a LOD threshold corresponding to the confidence of 0.90 is considered. If there is still no result, the result of the permutation test is not considered, and the threshold is manually lowered to 3.0; and if there is no interval corresponding to 3.0, the threshold is lowered to 2.5. Finally, the LOD threshold is selected as 2.5 to determine if the QTL on the chromosome is related to the pod-shattering trait. The QTL obtained by the invention is obtained when the LOD threshold is 2.5.

In embodiments, the invention provides the application of the soybean anti-pod-shattering major QTL or the soybean anti-pod-shattering major QTL obtained by the mapping method in studying the genetic mechanism of the pod-shattering trait or screening for molecular markers related to soybean yield. In the invention, the molecular marker is a molecular marker of the CAPS type. Directing at the difference loci of the two parents in the QTL interval, a CAPS (Cleaved Amplified Polymorphic Sequence, CAPS) molecular marker is developed for SNP loci, and the developed molecular marker is used to detect the RILs genotypes. The enzyme digestion information of the SNP loci is determined by using an online software dCAPS Finder 2.0 (helix.wustl.edu/dcaps/dcaps.html), where qPD05 has a restriction enzyme cutting site, and a CAPS marker is developed. The amplification primer for the CAPS molecule marker includes a forward primer and a reverse primer; the forward primer includes the following nucleotide sequences: (1) a nucleotide sequence included as shown in SEQ ID NO. 1 of the Sequence Listing; and (2) a nucleotide sequence obtained by nucleotide substitution, deletion and addition on the basis of the condition (1); and the reverse primer includes the following nucleotide sequences: A. a nucleotide sequence included as shown in SEQ ID NO. 2 of the Sequence Listing; and B. a nucleotide sequence obtained by nucleotide substitution, deletion and addition on the basis of the condition A. 20 µL of the reaction system of the amplification primer for the CAPS molecular marker includes 50 ng of genomic DNAs, a 10×PCR buffer, 2 mmol/L of dNTPs, 2 mmol/L of a primer, and 1 U Taq polymerase. The amplification procedure of the amplification primer for the CAPS molecular marker is: pre-denaturation at 94° C. for 4 min, denaturation at 94° C. for 30 s, annealing at 58° C. for 40 s, extension at 72° C. for 1 min, 34 cycles, and finally extension at 72° C. for 10 min, and storage at 4° C.

In embodiments, the invention provides the application of the soybean anti-pod-shattering major QTLqPD05 in map-based cloning.

In embodiments, the invention provides the application of the soybean anti-pod-shattering major QTLqPD05 in transgenic breeding of a pod-shattering gene.

In embodiments, the invention provides a soybean anti-pod-shattering gene obtained by screening based on the soybean anti-pod-shattering major QTLqPD05, including a DNA (cytosine-5) methyltransferase 3 coding sequence, a NAPD-dependent malic enzyme coding sequence, and a hypothetical protein coding sequence; where the DNA (cytosine-5) methyltransferase 3 coding sequence may include the following nucleotide sequences. (1) a nucleotide sequence included as shown in SEQ ID No. 3 of Sequence Listing; and (2) a nucleotide sequence obtained by nucleotide substitution, deletion and addition on the basis of the condition (1). The NAPD-dependent malic enzyme coding sequence includes the following nucleotide sequences: (a) a nucleotide sequence included as shown in SEQ ID No. 4 of Sequence Listing; and (b) a nucleotide sequence obtained by nucleotide substitution, deletion and addition on the basis of the condition (a). The hypothetical protein coding sequence includes the following nucleotide sequences: (I) a nucleotide sequence included as shown in SEQ ID No. 29 of Sequence Listing; and (II) a nucleotide sequence obtained by nucleotide substitution, deletion and addition on the basis of the condition (I).

In embodiments, the screening method may include the following steps: the parent Heihe 43 is an anti-pod-shattering material, and the parent Heihe 18 is a pod-shattering material, and the soybean anti-pod-shattering gene is obtained by screening out a gene with significant difference in expression level between the two parents via analysis of the expression of genes within the QTL interval in the pods of the two parents during the R6 period.

In embodiments, the amplification primer of the DNA (cytosine-5) methyltransferase 3 coding sequence includes a forward primer and a reverse primer; the nucleotide sequence of the forward primer is shown in SEQ ID No. 5 of Sequence Listing; and the nucleotide sequence of the reverse primer is shown in SEQ ID No. 6 of Sequence Listing. The NAPD-dependent malic enzyme coding sequence includes a forward primer and a reverse primer; the nucleotide sequence of the forward primer is shown in SEQ ID No. 7 of Sequence Listing; and the nucleotide sequence of the reverse primer is shown in SEQ ID No. 8 of Sequence Listing. The hypothetical protein coding sequence includes a forward primer and a reverse primer; the nucleotide sequence of the forward primer is shown in SEQ ID No. 9 of Sequence Listing; and the nucleotide sequence of the reverse primer is shown in SEQ ID No. 10 of Sequence Listing. Amplification of the soybean anti-pod-shattering gene may adopt a two-step PCR reaction procedure: the first step being pre-denaturation: 95° C., 30 s; and the second step being PCR reaction: 95° C., 5 s; 60° C., 31 s, for 40 cycles.

In embodiments, the invention also provides the application of the soybean anti-pod-shattering gene in selection of anti-pod-shattering varieties of soybean.

In some embodiments, the soybean anti-pod-shattering major QTLqPD05 and the mapping method and application thereof as provided by the invention will be described in detail in connection with the following embodiments, but they should not be construed as limiting the claimed scope of the invention.

Embodiment 1

Plant Materials and Identification of Pod-Shattering Phenotypes

A mapping population containing 260 strains of RIL7 was configured by crossing between Heihe 43 as the female parent and Heihe 18 as the male parent. The obtained 260 strains of RIL7 of the fifth and sixth generations as well as the two parents thereof were simultaneously planted in a soybean test field at Heihe Branch of Heilongjiang Academy of Agricultural Sciences respectively in 2015 and 2016, where the planting environments of the two years were named 1A and 1B, respectively. The parents were replicated for 3 times in 4 rows, and the materials of the offspring group were arranged in a random plot design, with a row length of 4 m, a row spacing of 66.7 cm, and a plant spacing of 5 cm. The plants were subjected to manual spot seeding. The female parent, Heihe 43, was the variety having the largest planting area in the early-maturing region of Heilongjiang Province. This highly anti-pod-shattering variety was prepared by hybrid breeding through a pedigree method, with the Heihe 18 as the female parent and the Heihe 23 as the male parent. The male parent, Heihe 18, was a variety of a type sensitive to pod shattering. Although the difference in agronomic traits between Heihe 18 and Heihe 43 was not significant, the pod shattering phenomenon of Heihe 18 was extremely obvious (Dezhi Han et al. 2015).

The pod-shattering rate was the main evaluation index for the identification of soybean pod-shattering phenotypes, where the pod-shattering rate=(the number of shattered pods/the number of total pods)×100% (Peng Yuhua et al. 1991). Asian Vegetable Research and Development Center (AVRDC) graded the pod-shattering phenotypes of soybean based on the pod-shattering rates, where the pod-shattering rate of 0% was set as grade 1 (high anti-pod-shattering), the pod-shattering rate between 0-10% was set as grade 2 (anti-pod-shattering), the pod-shattering rate between 11-25% was set as grade 3 (moderate anti-pod-shattering), the pod-shattering rate between 26-50% was set as grade 4 (moderate pod-shattering), and the pod-shattering rate above 50% was set as grade 5 (serious pod-shattering).

This embodiment may be employed an indoor drying method to determine the pod-shattering rate. The soybean pods at the full-ripe stage (R8) were cut with a scissor, and sealed in a ziplock bag (to prevent evaporation of water) and refrigerated in a refrigerator at 4° C. to serve as a sample. In order to ensure the reliability of the data, it was avoided to touch the pods when samples were picked, so as to keep the consistency of the test materials before detection as far as possible. We set the oven temperature to 80° C. and the drying time to 5 h as the optimum detection conditions for identifying the pod-shattering rate. In order to ensure the safety of the test, the experimental materials were placed in a high-temperature resistant wide-mouthed glass cup for the drying experiment. Before the start of the test, the oven was preheated to a treatment temperature in advance, the material was quickly taken out at the investigation time, and meanwhile the oven door was quickly closed (Dezhi Han et al. 2015). The difference in the pod-shattering rate between Heihe 18 and Heihe 43 is extremely significant during manual detection. According to the AVRDC evaluation criteria, the Heihe 43 had the pod-shattering of Grade 2 (medium anti-pod-shattering), and the Heihe 18 had the pod-shattering of Grade 4 (medium pod-shattering), which was substantially consistent with the natural pod-shattering conditions (Dezhi Han et al. 2015).

Results

Figure 1B:
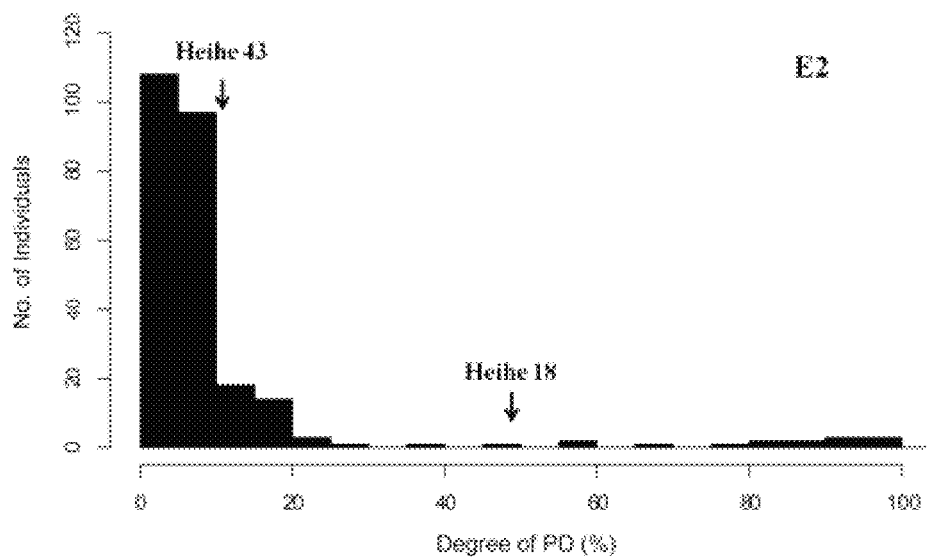
FIG. 1B shows the pod-shattering rates of 260 RILs and two parents thereof in Heihe of Heilongjiang Province in 2016.

The pod-shattering rates of 260 RILs and two parents thereof in Heihe of Heilongjiang Province in 2015 (1A) and 2016 (1B) were identified (FIG. 1). During the two years, Heihe 18 showed a higher pod-shattering rate than that of Heihe 43, respectively of 37% versus 3%, and 47.03% versus 11.36%. During the two years, the distribution of pod-shattering rates of RILs was presented as a continuous distribution, but it did not conform to the normal distribution, and showed a skewed distribution biased to the female parent Heihe 43 (FIG. 1), indicating that the allele carried by the female parent Heihe 43 played the role of anti-pod-shattering. There was no obvious transgressive inheritance in the offspring. FIG. 1 showed the pod-shattering rates of the female parent Heihe 43 and the male parent Heihe 18 during the two years with arrows. 1A and 1B represented the planting environments at Heihe in 2015 and 2016, respectively.

Embodiment 2

DNA Extraction

Placed into a 2.0 mL centrifuge tube was an appropriate amount of soybean tender leaves (about 0.1 g), added with steel beads, and cooled in liquid nitrogen, thereafter the leaves were ground by a sample making machine and then stored at −80° C. until use. The Soybean leaf DNA was extracted using a modified CTAB method (Saghaimaroof et al. 1984). The extracted DNA was subjected to mass detection by using 0.8% agarose gel electrophoresis and an ultraviolet spectrophotometer.

Embodiment 3

Constructing and Sequencing of SLAF (Specific-Locus Amplified Fragments) Libraries SLAF-library construction and sequencing were performed on 260 RILs and two parents thereof. Prediction of enzyme digestion was conducted by selecting the soybean Williams 82 v2.1 genome (phytozome.jgi.doe.gov) as a reference genome, where the combination of RsaI enzyme digestion and HaeIII enzyme digestion was selected to cleave the genomic DNA of each sample. A sequence having an enzyme-digested fragment length of 364-414 bp was defined as a SLAF tag, and it was predicted that 132,516 SLAF tags may be obtained. The obtained enzyme-digested fragments (SLAF tags) were subjected to the treatment of A addition at the 3' terminus, connection with Dual-index sequencing linker, PCR amplification, purification, sample mixing, and target-fragment selecting through gel excision, and then a sequencing library was constructed. The library was qualified and then sequenced for paired ends (125 bp) by using Illumina HiSeq. In order to evaluate the accuracy of the library-construction experiment, *Oryza sativa* L *japonica* was used as a control to be subjected to the same treatment and participate in library construction and sequencing. The enzyme digestion efficiency was evaluated by the alignment efficiency of the control data, so as to judge the accuracy and effectiveness. The SLAF tags were developed in parents and progenies by clustering of the reads, and the polymorphic SLAF tags were screened.

Embodiment 4

SLAF-seq Polymorphic Analysis and Genotyping

The SLAF-seq data grouping and genotyping of the samples were performed according to the following procedure. The original sequencing read length of the SLAF-seq library was 125 bp at the end. In order to ensure the quality of information analysis, the original sequencing data was filtered. The criteria for filtering of the original data was as follows: filtering out a reads containing a linker sequence; filtering out a reads having a N content exceeding 10% of the length of the reads; where since the first few bps of the sequencing reads were the residue left by the enzyme digestion of fragments and has a lower sequencing quality at the end, 4-103 bp in the middle of the reads were selected for data analysis. The filtered sequencing reads were aligned to the reference genome by using the BWA software, where a reads that has paired ends aligned to a reads at the same position is of the same SLAF tag. Polymorphic analysis was conducted according to the differences in the number of alleles and the gene sequences, and the SLAF tags were classified. The SLAF tags were mapped to the reference genome, and the SLAF tags and polymorphic SLAF tags on different chromosomes were counted. A distribution map of the SLAF tags and the polymorphic SLAF tags on the chromosomes was drawn according to the distribution of the SLAF tags on the chromosomes.

In order to facilitate subsequent genetic analysis, in this embodiment genotype encoding of the polymorphic tags was conducted, and the polymorphic tags were divided into eight separation models (ab×cd, ef×eg, hk×hk, lm×ll, nn×np, aa×bb, ab×cc, and cc×ab) according to the biallelic encoding rule commonly used in genetics. The type of aa×bb was suitable for inbred populations (such as F2, RIL, DH), and the remaining markers were suitable for hybrid populations. The population used in the invention was RIL, the parental genotypes were aa (male parent) and bb (female parent), and the progeny genotype is ab, indicating that the sample was heterozygous in terms of the encoding type of the marker, where one of genotypes was derived from the male parent, and the other one of the genotypes was derived from the female parent. In order to ensure the quality of the genetic map, the polymorphic SLAF tags were filtered according to the following rules: 1) filtering out a polymorphic SLAF tag having a parental sequencing depth below 10×; and 2) filtering out a polymorphic SLAF tag for which the number of SNPs was greater than 5. Since the sequencing length of the SNP tag was 200 bp, occurring of too many SNPs was considered as a high-frequency variation region in sequencing. 3) integrity filtering. Markers that at least cover more than 70% of genotype individuals in all progenies were screened. The loci of which the parental information was missing was filtered out based on the detection results of the parental genotypes, and finally the obtained polymorphic SLAF tags were used to construct a high-density genetic map. The content of this part was entrusted to Biomarker Technologies to complete.

Figure 2A:
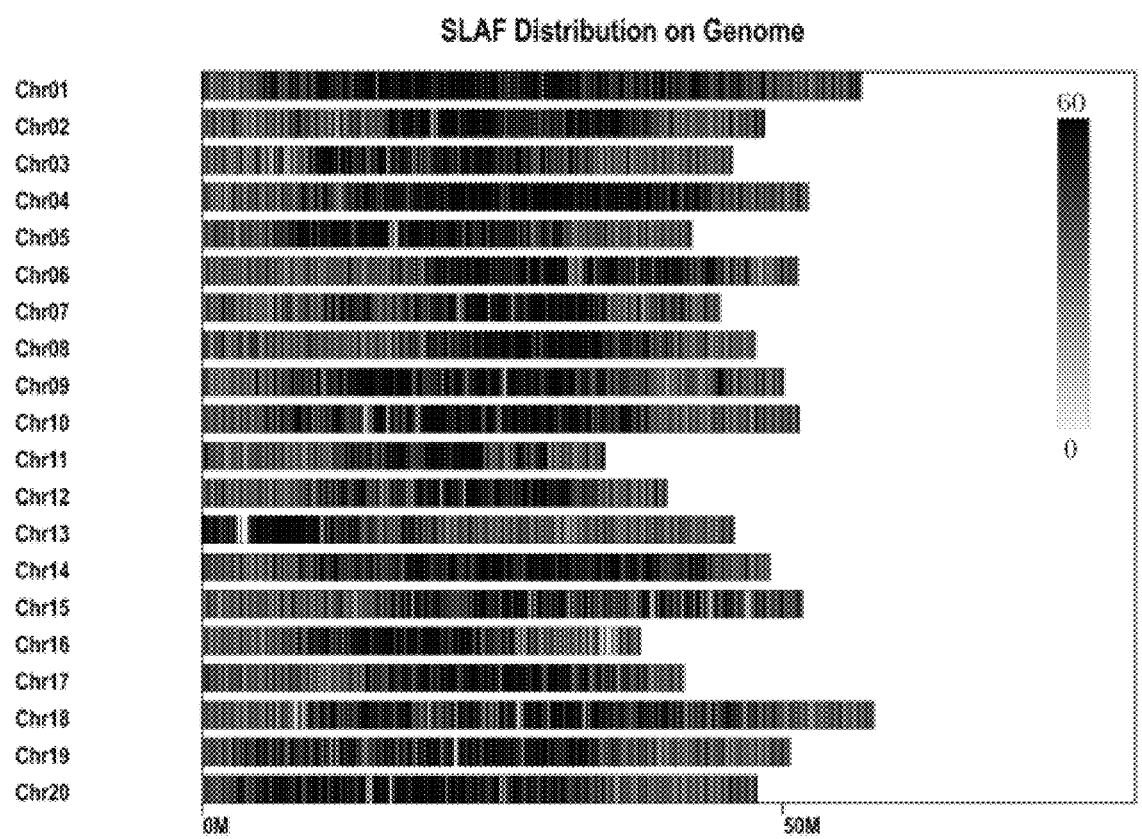
FIG. 2 shows the distribution of a SLAF tag and a polymorphic SLAF tag on a chromosome. wherein FIG. 2-A is a diagram showing the distribution of the SLAF tag, and FIG. 2-B is a diagram showing the distribution of the polymorphic SLAF tag.
Figure 2B:
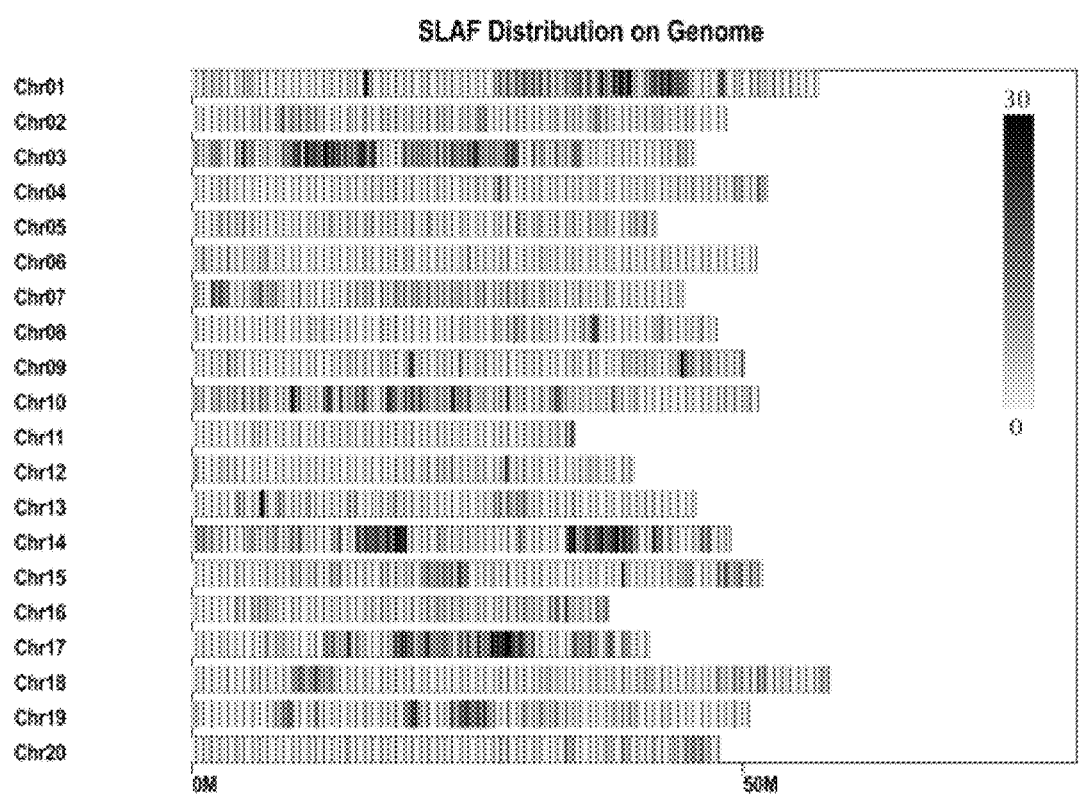

Genotyping was conducted on the two parents and the RIL population using SLAF-Seq. The enzyme digestion efficiency was 89.82%, indicating that the enzyme digestion efficiency was normal. The number of control sequencing reads obtained by us for evaluating the accuracy of experimental library construction was 398,386. The control sequencing reads was aligned to the reference genome with an alignment efficiency of 86.29%, and the alignment efficiency was substantially normal. The average Q30 of sequencing was 80.40%, and the average GC content was 38.12%. We had obtained 364,461 SLAF tags in total. The SLAF-tag sequencing depths of the two parents, Heihe 43 and Heihe 18, were 39.74× and 34.87×, respectively, and the numbers of SLAF tags were 195,279 and 205,644, respectively. The average SLAF-tag sequencing depth of the progeny was 12.35×. Polymorphic analysis was conducted on the obtained SLAF tags according to the differences in the number of alleles and the gene sequences, and 3 types of SLAF tags were obtained in total: polymorphic, non-polymorphic, and repetitive SLAF tags. The types of the tags developed by the SLAF technology were mainly SNP tags and Indel tags. There were 24,249 polymorphic SLAF tags in total, and the polymorphism ratio reached 6.65%. Genotyping was conducted on the obtained 24,249 polymorphic SLAF tags, and 11,028 tags were successfully genotyped. The material used in this study was the RIL7 population. Loci were selected such that the parental genotypes were homozygous and there was polymorphism between parents. The polymorphic tags of aa×bb type were selected as effective tags conforming to the characteristics of this population. The effective polymorphism of the genetic map constructed in this study was 2.68%. After filtering and quality evaluation, 5,227 SLAF tags available for construction of the high-density genetic map were obtained, and the types of the SLAF tags were all the aa×bb type. A distribution map of all of the SLAF tags and the polymorphic SLAF tags on the chromosomes was drawn according to the distribution of the SLAF tags on the chromosomes (FIG. 2). In FIG. 2, the horizontal axis was the length of the chromosome. where each yellow band represented a chromosome, the genome was divided based on the size of 1 M, and the color is darker when the number of SLAF tags in each window is more, and the color is lighter when the number of SLAF tags in each window is fewer; the darker area in the figure was the area where the SLAF tags were concentrated. FIG. 2-A was a diagram showing the distribution of the SLAF tag, and FIG. 2-B was a diagram showing the distribution of the polymorphic SLAF tag.

Embodiment 5

Construction of High-Density Genetic Map

After the obtained polymorphic SLAF tags were aligned to the reference genome for mapping, the SLAF tags were mapped to 20 chromosomes, and the tags each having a MLOD (the modified logarithm of odds) value relative to other SLAF tags below 5 were filtered out by calculating the MLOD value between pairwise tags. The screened tags were the Markers. Each chromosome was a linkage group. By using the linkage group as a unit, a linear arrangement of Markers in the linkage group was obtained by analyzing with a HighMap composition software, and the genetic distance between adjacent Markers is estimated, so as to finally obtain the high-density genetic map.

Figure 3:
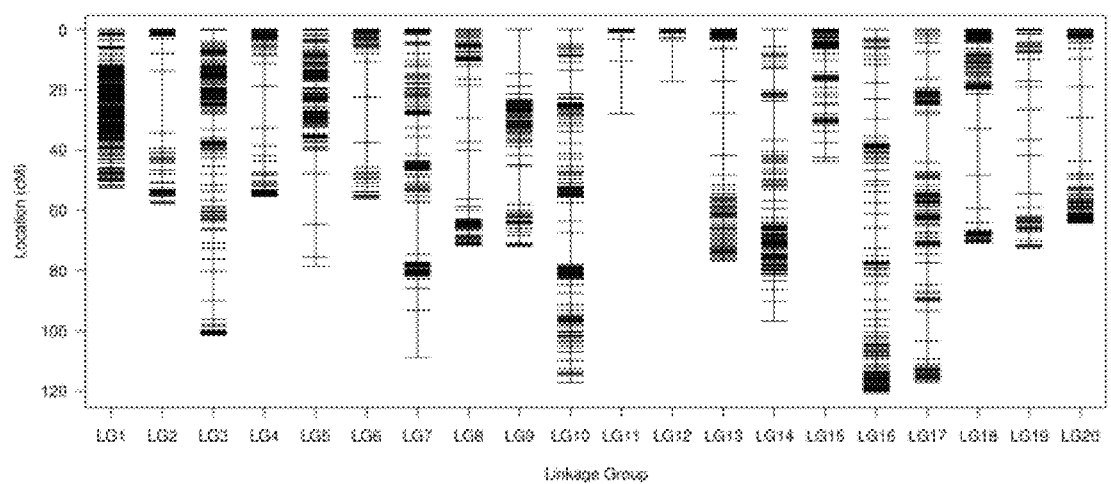
FIG. 3 is a high-density genetic map of the RIL population.
Figure 4:
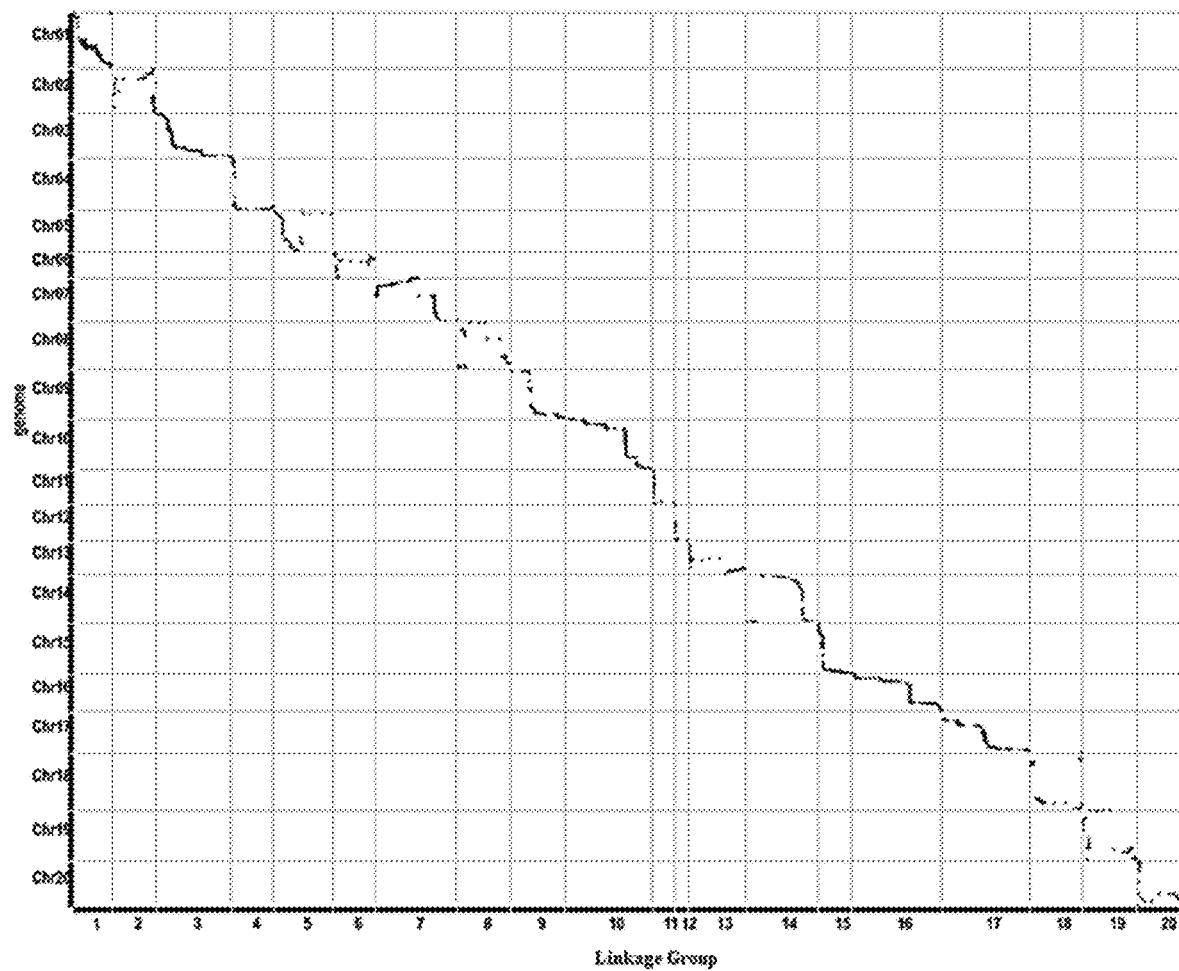
FIG. 4 is a genetic map and genomic collinearity analysis.

The screened 5,227 SLAF tags were divided into 20 linkage groups by mapping to the reference genome. by filtering out the tags each having a MLOD value relative to other SLAF tags below 5, a total of 4,593 Markers were obtained, and finally a genetic map with the total map distance of 1,478.86 cM was obtained (FIG. 3). The average genetic distance of the tags on the chromosomes was 0.53 cM. The average length of each chromosome was 73.94 cM. The chromosome with the highest number of tags was Gm03, which had 706 tags and a total length of 101.35 cM. The chromosome with the lowest number of tags was Gm12, which had 17 tags and a total length of 17.27 cM. Furthermore, the proportion of the inter-marker gap of less than 5 cM was found to be 95.72% (Table 1). The collinearity analysis of the positions of the Markers on the genome and the genetic map showed that the orders of most of the tags on the 20 chromosomes were consistent with those of the genome, indicating that the collinearity was good and the calculation accuracy of the genetic recombination rate was high (FIG. 4). Therefore, conducting gene annotation in the QTL interval was reliable. In FIG. 4, the horizontal axis was the genetic distance of each linkage group, and the vertical axis was the physical length of each linkage group, where the collinearity relationship of the Markers in the genome and the genetic map was represented in the form of scatter. The more diagonal relationship presented by the markers indicated that the collinearity between the genetic map and the genome was better. Different colors indicated different chromosomes or linkage groups. The content of this part was entrusted to Biomarker Technologies to complete.

The segregation distortion phenomenon was ubiquitous. The Markers of the invention contained 4,394 segregation distortion markers, accounting for 95.67% of the total number of markers, where the number of tags biased to the male parent Heihe 18 was 1,611, and the number of tags biased to the female parent Heihe 43 was 2,783. Polymorphic markers with partial segregation distortion (chi-square test, P<0.01) were selected for map construction.

TABLE 1

Information of high-density genetic map

| Chromosome | Number of tags[b] | Total map distance (cM) | Average map distance (cM) Average map distance | Gaps ≤ 5 | Maximum Gap (cM) |
|---|---|---|---|---|---|
| 1 | 489 | 52.51 | 0.11 | 100% | 2 |
| 2 | 66 | 57.71 | 0.89 | 95.38% | 20.61 |
| 3 | 706 | 101.35 | 0.14 | 99.57% | 9.75 |
| 4 | 103 | 55.26 | 0.54 | 96.08% | 13.8 |

TABLE 1-continued

Information of high-density genetic map

| Chromosome | Number of tags[b] | Total map distance (cM) | Average map distance (cM) Average map distance | Gaps ≤ 5 | Maximum Gap (cM) |
|---|---|---|---|---|---|
| 5 | 135 | 78.59 | 0.59 | 97.76% | 16.95 |
| 6 | 64 | 56.2 | 0.89 | 95.24% | 15.12 |
| 7 | 393 | 108.94 | 0.28 | 97.19% | 17.33 |
| 8 | 115 | 71.71 | 0.63 | 97.37% | 16.47 |
| 9 | 96 | 71.87 | 0.76 | 97.89% | 14.79 |
| 10 | 463 | 117.27 | 0.25 | 99.35% | 10.38 |
| 11 | 44 | 27.83 | 0.65 | 93.02% | 17.33 |
| 12 | 17 | 17.27 | 1.08 | 87.50% | 13.75 |
| 13 | 111 | 76.76 | 0.7 | 82.73% | 14.16 |
| 14 | 450 | 96.77 | 0.22 | 99.11% | 12.97 |
| 15 | 338 | 43.79 | 0.13 | 100% | 4.63 |
| 16 | 272 | 120.6 | 0.45 | 97.79% | 6.81 |
| 17 | 399 | 117.1 | 0.29 | 98.74% | 15.84 |
| 18 | 157 | 70.73 | 0.45 | 97.44% | 15.34 |
| 19 | 84 | 72.31 | 0.87 | 85.54% | 12.45 |
| 20 | 91 | 64.29 | 0.71 | 96.67% | 14.41 |
| Total | 4,593 | 1,478.86 | 0.53 | 95.72% | 20.61 |

Figure 5:
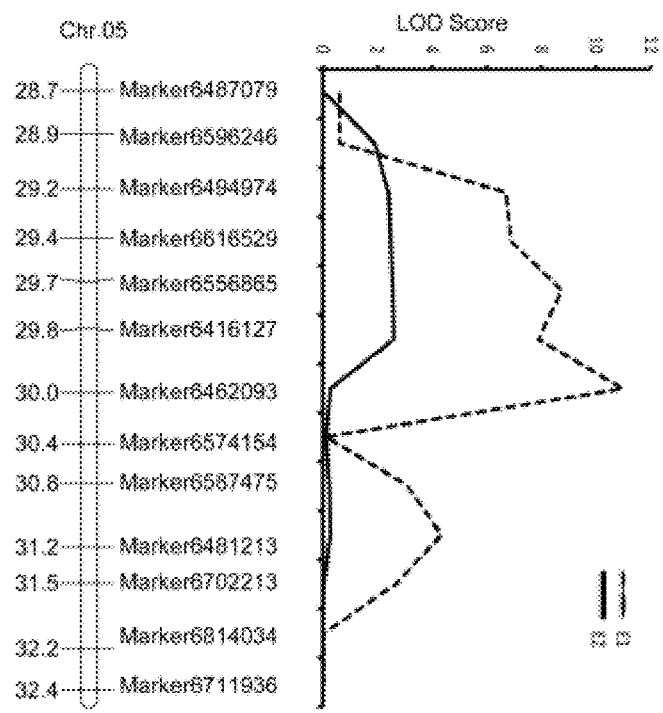
FIG. 5 shows the mapping of QTLs on chromosome 5.

The QTLs related to the anti-pod-shattering of RILs in two environments were detected by using the inclusive composite interval mapping method of a R/qtl software package. In this study, we detected a total of 4 related QTLs respectively located on the chromosomes 1, 5, and 8 (FIG. 5), and the explained phenotypic variation rate was ranged from 8.37% to 24.443% (Table 2). Among the 4 QTLs, each of 3 QTLs (qPD01, qPD05, qPD08-1) explained a higher phenotypic variation rate (>10%), where the QTLs (qPD05, qPD08-1) located on chromosomes 5 and 8 could be detected both in the two years, and thus may be considered as stable QTLs in the population of this study. The QTL (qPD01) located on chromosome 1 was only detected in 2016, which explained the phenotypic variation rate of 24.443% (Table 2). The additive effects of these QTLs were all negative values, indicating that the superior alleles were all derived from the female parent Heihe 43, and the alleles carried by the female parent Heihe 43 played a role in anti-pod-shattering.

TABLE 2

Soybean pod-shattering QTLs in different environments

| QTL[a] | Env[b] | Chr[c] | Flanking marker[d] | Interval[e](cM) | LOD[f] | ADD[g] | PVE[h](%) |
|---|---|---|---|---|---|---|---|
| qPD05 | 1A, 1B | 5 | 40448596-40703417 | 29.653-30.04 | 7.171 | −5.995 | 15.138 |

[a]the QTL name was a combination of soybean pod-shattering;
[b]Environment: 1A indicated the planting environment at Heihe in 2015, and 1B indicated the planting environment at Heihe in 2016;
[c]Chromosome;
[d]markers on both sides, markers on the left and right sides of the QTL;
[e]interval, a confidence interval between two markers;
[f]LOD, logarithm of odds;
[g]additive effect;
[h]the phenotypic variation rate explained by each QTL.

Embodiment 6

QTL Mapping of the Pod-Shattering Trait of Soybean

QTL mapping of pod-shattering related traits was carried out according to the soybean pod-shattering phenotypes in two environments by using the inclusive composite interval mapping method of a R/qtl software package. Threshold setting was performed by using a permutation test for 1000 times, where firstly a LOD threshold corresponding to the confidence of 0.99 was considered, and if there was no mapped interval, then a LOD threshold corresponding to the confidence of 0.95 was considered; and if there was no mapped interval, then a LOD threshold corresponding to the confidence of 0.90 was considered. If there was still no result, the result of the permutation test was not considered, and the threshold was manually lowered to 3.0; and if there was no interval corresponding to 3.0, the threshold was lowered to 2.5. Finally, the LOD value was selected as 2.5 to determine if the QTL on the chromosome was related to the pod-shattering trait. The content of this part was entrusted to Biomarker Technologies to complete.

Embodiment 7

Development and Application of Molecular Markers in the Interval of QTLs

Directing at the difference loci of the two parents in the QTL interval, in this embodiment a CAPS (Cleaved Amplified Polymorphic Sequence, CAPS) molecular marker was developed for SNP loci, and the developed molecular marker was used to detect the RILs genotypes. The enzyme digestion information of the SNP loci is determined by using an online software dCAPS Finder 2.0 (helix.wustl.edu/dcaps/dcaps.html), where qPD05 has a restriction enzyme cutting site, and a CAPS marker is developed. The endonuclease HpaII was selected as an enzyme for the candidate markers. PCR primers were designed on both sides of a candidate CAPS marker using a Primer 3.0 software (Table 3).

Using the genomic DNAs of the two parents and the 260 parts of RILs as templates, 20 μL of a PCR reaction system includes 50 ng of genomic DNAs, a 10×PCR Buffer, 2 mmol/L of dNTPs, 2 mmol/L of a primer and 1 U Taq polymerase (TransGen Biotech). The PCR amplification procedure is: pre-denaturation at 94° C. for 4 min, denaturation at 94° C. for 30 s, annealing at 58° C. for 40 s, extension at 72° C. for 1 min, 34 cycles, and finally extension at 72° C. for 10 min, and storage at 4° C. The PCR product was detected by 1.5% agarose gel electrophoresis. According to the (NEW ENGLAND BioLabs) enzyme digestion method, 10 μL of an enzyme digestion system including 5 μL of the PCR product, 0.2μ 10 U/μL of an enzyme, 1.5 μL of a buffer (NEB, www.neb.com/), and 3.3 μL of ddH2O, was used to conduct enzyme digestion in a constant-temperature water bath at 37° C. for 40 minutes. The digested product was detected by 2% agarose gel electrophoresis. The CAPS-labeled digested product was detected by 2% agarose gel electrophoresis product was detected by 1.5% agarose gel electrophoresis. According to the (NEW ENGLAND BioLabs) enzyme digestion method, 10 μL of an enzyme digestion system including 5 μL of the PCR product, 0.2μ 10 U/μL of an enzyme, 1.5 μL of a buffer (NEB, www.neb.com/), and 3.3 μL of ddH2O, was used to conduct enzyme digestion in a constant-temperature water bath at 37° C. for 40 minutes. After the digested product was detected by 2% agarose gel electrophoresis, 3 digested fragments were theoretically produced through HpaII enzyme digestion from the PCR fragments generated by the CAPS marker in the qPD05

TABLE 3

Information of primer sequence

| QTL | Type of marker | Mutation site | Physical location | Endonuclease | Sequence of Primer (5'-3') | Fragment Length (bp) | Length of enzyme-digested fragment (bp) |
|---|---|---|---|---|---|---|---|
| qPD05 | CAPS | A/G | 40448939 | HpaII | F: CCTAGCTATTTCATCT TCACGA (SEQ ID No: 1) R: AATCCTTACAACGTAC GTGTGT (SEQ ID No. 2) | 540 | 540(A)/294 + 246(G) |

In this embodiment, directed to the difference loci in the QTL interval, PCR amplification of the two parents was performed by using the designed primers (Table 3), and individual PCR products each having a size similar to the length of the target fragment were obtained. An analysis of alignment to the Williams 82 reference sequence revealed that, the two parents had differences in the target SNP position, which was consistent with the prediction. 3 digested fragments were theoretically produced through HpaII enzyme digestion from the PCR fragments generated by the CAPS marker in the qPD05 interval. Since two digested fragments were similar in length, the agarose gel electrophoretogram cannot separate two bands, and thus only 2 types of digested products were detected. The DNA fragment not subjected to the digestion reaction had a size of 540 bp, and the allelic variation was A; and the DNA fragment subjected to the digestion reaction had sizes of 294 bp and 246 bp, and the allelic variation was G. It had been determined that the identification of the two parents on the 4 SNP and Indel loci was correct, indicating that the developed CAPS marker could be used for the genotype identification of the 260 parts of RILs progenies.

Embodiment 8

Development and Application of Molecular Markers in the Interval of the QTLs on Chromosome 5

The developed molecular marker was used to identify the genotypes of 36 parts of cultivated soybeans and 36 parts of wild soybeans. The primer sequences were primers used in the development of the molecular marker. Using the genomic DNAs of the 36 parts of cultivated soybeans and the 36 parts of wild soybeans as templates, 20 μL of a PCR reaction system includes 50 ng of genomic DNAs, a 10×PCR Buffer, 2 mmol/L of dNTPs, 2 mmol/L of a primer and 1 U Taq polymerase (TransGen Biotech). The PCR amplification procedure is: pre-denaturation at 94° C. for 4 min, denaturation at 94° C. for 30 s, annealing at 58° C. for 40 s, extension at 72° C. for 1 min, 34 cycles, and finally extension at 72° C. for 10 min, and storage at 4° C. The PCR interval. Since two digested fragments were similar in length, the agarose gel electrophoretogram cannot separate two bands, and thus only two types of digested products were detected. The DNA fragment not subjected to the digestion reaction had a size of 540 bp, and the allelic variation was A; and the DNA fragment subjected to the digestion reaction had sizes of 294 bp and 246 bp, and the allelic variation was G.

As identified, among the 36 parts of cultivated soybeans, 8 parts of the materials could be digested, with the genotype of G, and 28 parts of the materials could not be digested, with the genotype of A. Among the 36 parts of wild soybeans, 18 parts of the materials could be digested, with the genotype of G, and 18 parts of the materials could not be digested, with the genotype of A.

It could be seen from the above that, the genotypes of 18 parts of fresh edible soybeans were identified using the developed molecular marker. As identified, among the 18 parts of fresh edible soybeans, 10 parts of the materials could be digested, with the genotype of G, and 8 parts of the materials could not be digested, with the genotype of A.

Embodiment 9

Exploration of an Anti-Pod-Shattering Gene

The parent Heihe 43 was an anti-pod-shattering material, and the parent Heihe 18 was a pod-shattering material, and the candidate genes were further screened at a transcriptome level by screening out a gene with significant difference in expression level between the two parents via analysis of the expression of genes within the QTL interval in the pods of the two parents during the R6 period.

The specific implementation was as follows: the CDS sequences of the genes in the mapping interval were extracted at Phytozome (phytozome.jgi.doe.gov/pz/-portal.html#!search?show=KEYWORD&method=Org_Gmax), and the expression analysis primer was designed by using a Primer5 software (Table 4). The RNA of a soybean pod tissue was extracted according to the operation instruction of RNAprep Pure Plant Total RNA Extraction Kit (Cat No.:

DP432) of TIANGEN. The RNA of the soybean pod tissue was reverse-transcribed into a double-stranded cDNA by utilizing the operation instruction of a FastQuant RT Kit (Cat No.: KR106) reverse transcription kit, and the expression analysis was completed on a fluorescence quantitative PCR instrument ABI7300. The specific reaction system refers to a SYBR Premix Ex Taq (Cat No.: RR420A) of Takara, and a two-step PCR reaction procedure was adopted: the first step being pre-denaturation: 95° C., 30 s; and the second step being PCR reaction: 95° C., 5 s; 60° C., 31 s, for 40 cycles.

Embodiment 10

Application of Anti-Pod-Shattering Gene in Breeding Selection

The three genes developed in Embodiment 9 could be used separately or in combination as gene resources for controlling the anti-pod-shattering trait. By utilizing analysis of the anti-pod-shattering gene, a SNP difference existed between anti-pod-shattering and pod-shattering germplasms, and genotypic difference also existed in the hybrid

TABLE 4

List of information about qRT-PCR primers

| Gene ID | Primer sequence (5' to 3') | Sequence No. | Amplification Length (bp) |
|---|---|---|---|
| Glyma.05g005600 | F: ggatgatgtaagggagctagac<br>R: tcatcgatatttggccgacata | SEQ ID No. 5<br>SEQ ID No. 6 | 214 |
| Glyma.05g225900 | F: gcaacttttgtatccgtgctaa<br>R: gacttcttcgtgtgagaaaagc | SEQ ID No. 9<br>SEQ ID No. 10 | 182 |
| Glyma.05g226000 | F: tgacacaagccaatttacacag<br>R: cacccatttcatgaactgttgt | SEQ ID No. 11<br>SEQ ID No. 12 | 253 |
| Glyma.05g226400 | F: gaacatcacaggttattcggtg<br>R: tgttgagccaaaggagtgatat | SEQ ID No. 13<br>SEQ ID No. 14 | 167 |
| Glyma.05g226500 | F: aagacttgatgctgggctggtgg<br>R: gttttattttgttgtccctgtgg | SEQ ID No. 15<br>SEQ ID No. 16 | 95 |
| Glyma.05g227200 | F: agagtgaaggactatgtcaacg<br>R: ttcagtgtcatctcactctacg | SEQ ID No. 17<br>SEQ ID No. 18 | 202 |
| Glyma.05g227300 | F: gtccaaggaacatctaatgaagctg<br>R: cactcctttttgtttcattctctcg | SEQ ID No. 19<br>SEQ ID No. 20 | 132 |
| Glyma.05g227400 | F: ggctctaacaaggatgtgtttc<br>R: gcaaatgaaacgacttgagtca | SEQ ID No. 7<br>SEQ ID No. 8 | 182 |
| Glyma.05g228100 | F: gcgtcactgtcgcagtcgtcatc<br>R: ctccccactcgggtcgggtattt | SEQ ID No. 21<br>SEQ ID No. 22 | 147 |
| Glyma.05g228400 | F: tgcttgttggaggtattttgtg<br>R: gatcctcaaattcagcttcgac | SEQ ID No. 23<br>SEQ ID No. 24 | 129 |
| Glyma.05g228600 | F: aataattctaatacctttttacc<br>R: caagagtctgattctgacatctc | SEQ ID No. 25<br>SEQ ID No. 26 | 95 |
| Glyma.05g229100 | F: tactcatcatcatacgcagctt<br>R: ccatcttgctgtattagttggc | SEQ ID No. 27<br>SEQ ID No. 28 | 120 |

Figure 6:
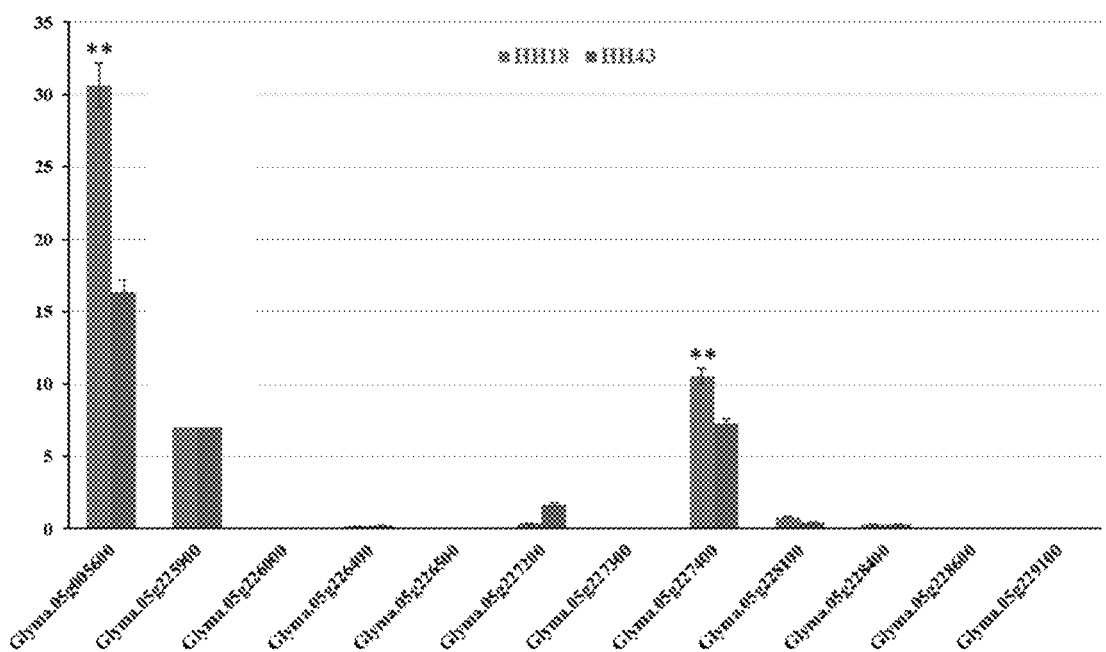
FIG. 6 is an analysis of the expression level of each soybean anti-pod-shattering candidate gene of the invention.

The expression analysis results were shown in FIG. 6. As can be seen from FIG. 6, in this interval the expression levels of three genes, i.e., Glyma.05g005600 (encoding the DNA cytosine-5-methyltransferase 3), Glyma.05g225900 (an unknown protein) and Glyma.05g227400 (the NAPD-dependent malic enzyme) in the pods of the anti-pod-shattering and pod-shattering parents were significantly different, so that the three genes were taken as candidate genes for controlling the anti-pod-shattering trait in this interval.

Figure 7:
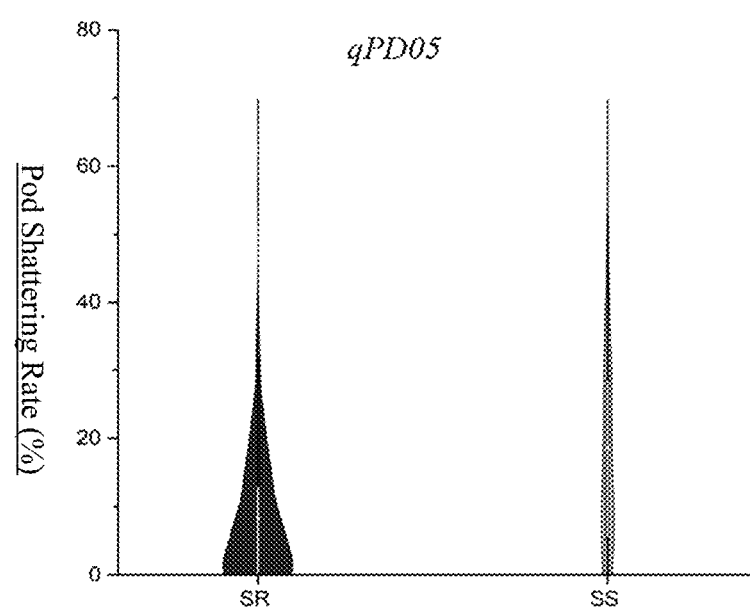
FIG. 7 is a violin plot of the qPD05 in offspring of 260 RILs.

The variance analysis of phenotype and genotype was carried out on 260 RILs. The violin plot of the qPD05 in offspring of 260 RILs was shown in FIG. 7. The results showed that there were 220 individuals carrying the anti-pod-shattering genotype, with an average pod-shattering rate of 8.57%; and there were 40 individuals carrying the pod-shattering genotype, with an average pod-shattering rate of 22.11%. There was a very significant difference in pod-shattering rate between individuals of the two genotypes (P=0.00087).

offspring, which was significantly correlated with the pod-shattering phenotype. That is, the anti-pod-shattering property could be selected by using the anti-pod-shattering genotype, thus realizing the application of the soybean anti-pod-shattering gene in germplasm resource screening and variety breeding.

In some embodiments, a high-density genetic linkage map covering the whole genome of soybean may be constructed by using a material of a RIL7 population which has pod-shattering soybean and anti-pod-shattering soybean as the parents, and QTL mapping of the anti-pod-shattering trait may be carried out on this population to obtain QTLs related to anti-pod-shattering.

In other embodiments, the construction of the high-density genetic linkage map and the identification of the novel QTLs related to anti-pod-shattering specific to this population provide a reference for QTL mapping of soybean, map-based cloning, transgenic breeding of a pod-shattering gene, molecular-marker development and breeding applications, and meanwhile the soybean anti-podshattering gene provides a basis for selection of anti-pod-shattering varieties of soybean.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The foregoing descriptions are only some implementation manners of the invention. It should be noted that for a person of ordinary skill in the art, several improvements and modifications may further be made without departing from the principle of the invention. These improvements and modifications should also be deemed as falling within the protection scope of the invention.

To facilitate understanding the invention, the invention is described in more detail with reference to the appended drawings. These drawings depict some embodiments of the invention, this invention may, however, be embodied in many different forms and should not be construed as limited to the exemplary embodiments set forth herein. Rather, these embodiments are provided so that this disclosure will be thorough and complete.

---

What is claimed is:

1. A method for identifying a genotype of recombinant inbred lines (RILs) in soybeans with pod-shattering trait, comprising steps of:
   (1) mapping soybean anti-pod-shattering major quantitative trait locus (QTL) using two soybean parent plants and resulting RILs;
   (2) performing PCR amplification using genomic DNAs of the two soybean parent plants and the resulting RILs as templates and with
       a forward primer comprises a nucleotide sequence as shown in SEQ ID NO. 1 and
       a reverse primer comprises a nucleotide sequence as shown in SEQ ID NO. 2;
   (3) digesting PCR fragments generated in step (2) with HpaII to produce digested fragments; and
   (4) determining the genotype of RILs based on presence of target digested fragments in the digested fragments in step (3);
   wherein the major QTL in step (1) is mapped on chromosome 5 of the soybeans.

2. The method according to claim 1, wherein the step (1) comprises:
   (1.1) constructing recombinant inbred lines of fifth and sixth generations by using pod-shattering soybean and anti-pod-shattering soybean as parents, simultaneously sowing the pod-shattering soybean, the anti-pod-shattering soybean and the recombinant inbred line of a fifth-generation, and simultaneously sowing the pod-shattering soybean, the anti-pod-shattering soybean and the recombinant inbred line of a sixth-generation, to obtain samples of the pod-shattering soybean, the anti-pod-shattering soybean and the soybean recombinant inbred lines;
   (1.2) respectively extracting DNAs from samples of the pod-shattering soybean, the anti-pod-shattering soybean and the soybean recombinant inbred lines, to obtain genomic DNAs of the pod-shattering soybean, the anti-pod-shattering soybean and the soybean recombinant inbred lines;
   (1.3) respectively constructing specific locus amplified fragment (SLAF) libraries by utilizing the genomic DNA of each of the samples of the pod-shattering soybean, the anti-pod-shattering soybean and the soybean recombinant inbred lines, and separately sequencing the constructed SLAF libraries to obtain original sequencing data;
   (1.4) filtering the original sequencing data to select 4-103 bp in the middle of each reads as analysis data;
   (1.5) aligning the analysis data to a reference genome, wherein each reads that has paired ends aligned to a reads at a same position is of a same SLAF tag, and then conducting polymorphic analysis of the SLAF tags according to differences in number of alleles and gene sequences to obtain polymorphic SLAF tags;
   (1.6) filtering the polymorphic SLAF tags to obtain screened polymorphic SLAF tags;
       wherein the filtering is to delete the polymorphic SLAF tags having the following conditions:
           a. a polymorphic SLAF tag having a parent sequencing depth below 10×;
           b. a polymorphic SLAF tag containing more than 5 SNP loci; and
           c. a polymorphic SLAF tag that is insufficient to cover 70% of genotype individuals in all progenies;
   (1.7) aligning the screened polymorphic SLAF tags with a reference genome for mapping, wherein the screened polymorphic SLAF tags are mapped to 20 chromosomes, and using each chromosome as a linkage group to calculate a genetic distance between adjacent polymorphic SLAF tags on each linkage group, so as to obtain a high-density genetic map; and
   (1.8) conducting QTL mapping of pod-shattering phenotypes and pod-shattering traits of soybeans by employing an inclusive composite interval mapping method according to the high-density genetic map, so as to obtain interval qPD05 of soybean anti-pod-shattering major QTLs.

3. The method according to claim 2, wherein the number of the samples of soybean recombinant inbred lines in step (2) is 200-300.

4. The method according to claim 2, wherein in step (1) the pod-shattering soybean is used as a male parent; and the anti-pod-shattering soybean is used as a female parent.

5. The method according to claim 2, wherein variety of the pod-shattering soybean is Heihe 18; and variety of the anti-pod-shattering soybean is Heihe 43.

6. The method according to claim 2, wherein in step (3), during the separate sequencing the sequencing depth of the SLAF library of the pod-shattering soybean is 39.74×; the sequencing depth of the SLAF library of the anti-pod-shattering soybean is 34.87×; and the sequencing depth of the SLAF library of the soybean recombinant inbred line is 12.35×.

7. The method according to claim 2, wherein in step (4), filtration criteria are as follows: filtering out a reads containing a linker sequence; and filtering out a reads having a N content exceeding 10% of a length of the reads.

8. The method according to claim 2, wherein in step (7), before the calculation of the genetic distance, the method further comprises performing second filtering on the polymorphic SLAF tags; wherein criterion for the second filtering is to calculate a modified logarithm of odds (MLOD) value between pairwise polymorphic SLAF tags and then filter out polymorphic SLAF tags each with a MLOD value below 5.

* * * * *

SEQUENCE LISTING

```
<160> NUMBER OF SEQ ID NOS: 29

<210> SEQ ID NO 1
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 1
cctagctatt tcatcttcac ga                                          22

<210> SEQ ID NO 2
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 2
aatccttaca acgtacgtgt gt                                          22

<210> SEQ ID NO 3
<211> LENGTH: 214
<212> TYPE: DNA
<213> ORGANISM: Artificial Sequence
<220> FEATURE:
<223> OTHER INFORMATION: Synthetic nucleic acid sequence

<400> SEQUENCE: 3
ggatgatgta agggagctag acggtgatcg cttggaacag ctgatgagca catttggtgg    60
ttttgatcta attgttggtg gcagtccatg taataacctg gctggtagca acagggtcag   120
ccgggatgga ctggagggaa aagaatcttc tctcttcttt gattatttta ggattctaga   180
cttggtaaaa aatatgtcgg ccaaatatcg atga                              214

<210> SEQ ID NO 4
<211> LENGTH: 182
<212> TYPE: DNA
<213> ORGANISM: Artificial Sequence
<220> FEATURE:
<223> OTHER INFORMATION: Synthetic nucleic acid sequence

<400> SEQUENCE: 4 gcaactttg tatccgtgct aactaaaaga gggagtttcc ttggaggctc cagaacttcc     60
ttttctgtac agaagaactt ttgatatcca accttgttaa ttagagctta gttaatattt   120
```

```
catgcacaaa atagggaaaa ttttgagtcc ctcaccttca gcttttctca cacgaagaag    180
tc                                                                   182

<210> SEQ ID NO 5
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 5
ggatgatgta agggagctag ac                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 6
tcatcgatat ttggccgaca ta                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 7
ggctctaaca aggatgtgtt tc                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 8
gcaaatgaaa cgacttgagt ca                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 9 gcaactttttg tatccgtgct aa                                             22

<210> SEQ ID NO 10
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 10
gacttcttcg tgtgagaaaa gc                                              22

<210> SEQ ID NO 11
```

```
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 11
tgacacaagc caatttacac ag                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 12
cacccatttc atgaactgtt gt                                              22

<210> SEQ ID NO 13
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 13
gaacatcaca ggttattcgg tg                                              22

<210> SEQ ID NO 14
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 14
tgttgagcca aaggagtgat at                                              22

<210> SEQ ID NO 15
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 15
aagacttgat gctgggctgg tgg                                             23

<210> SEQ ID NO 16
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 16
gttttatttt gttgtccctg tgg                                             23

<210> SEQ ID NO 17
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 17
```

-continued agagtgaagg actatgtcaa cg                                    22

<210> SEQ ID NO 18
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 18
ttcagtgtca tctcactcta cg                                    22

<210> SEQ ID NO 19
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 19
gtccaaggaa catctaatga agctg                                 25

<210> SEQ ID NO 20
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 20
cactcctttt tgtttcattc tctcg                                 25

<210> SEQ ID NO 21
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 21
ctccccactc gggtcgggta ttt                                   23

<210> SEQ ID NO 22
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 22
tgcttgttgg aggtattttg tg                                    22

<210> SEQ ID NO 23
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 23
tgcttgttgg aggtattttg tg                                    22

<210> SEQ ID NO 24
<211> LENGTH: 22
<212> TYPE: DNA

<213> ORGANISM: Artificial Sequence
<220> FEATURE:
<223> OTHER INFORMATION: Synthetic nucleic acid sequence

<400> SEQUENCE: 24
gatcctcaaa ttcagcttcg ac        22

<210> SEQ ID NO 25
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 25
aataattcta atacctttt acc        23

<210> SEQ ID NO 26
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 26
caagagtctg attctgacat ctc       23

<210> SEQ ID NO 27
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 27
tactcatcat catacgcagc tt        22

<210> SEQ ID NO 28
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 28
ccatcttgct gtattagttg gc        22

<210> SEQ ID NO 29
<211> LENGTH: 182
<212> TYPE: DNA
<213> ORGANISM: Artificial Sequence
<220> FEATURE:
<223> OTHER INFORMATION: Synthetic nucleic acid sequence

<400> SEQUENCE: 29 gcaactttg tatccgtgct aactaaaaga gggagtttcc ttggaggctc cagaacttcc      60
ttttctgtac agaagaactt tgatatcca accttgttaa ttagagctta gttaatattt    120
catgcacaaa atagggaaaa ttttgagtcc ctcaccttca gcttttctca cacgaagaag   180
tc                                                                  182